US006794359B2

United States Patent
Kramer et al.

(10) Patent No.: US 6,794,359 B2
(45) Date of Patent: Sep. 21, 2004

(54) VERTEBRATE INTESTINAL PROTEIN WHICH ABSORBS CHOLESTEROL, ITS INHIBITORS AND MEHTOD OF IDENTIFYING THE SAME

(75) Inventors: Werner Kramer, Mainz-Laubenheim (DE); Heiner Glombik, Hofheim (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 155 days.

(21) Appl. No.: 09/939,793

(22) Filed: Aug. 28, 2001

(65) Prior Publication Data

US 2002/0039774 A1 Apr. 4, 2002

(30) Foreign Application Priority Data

Aug. 29, 2000 (DE) .......................................... 100 42 447

(51) Int. Cl.[7] .............................................. A61K 38/00
(52) U.S. Cl. .......................................... 514/2; 514/368
(58) Field of Search ...................................... 514/2, 368

(56) References Cited

U.S. PATENT DOCUMENTS 5,872,141 A * 2/1999 Umbreit et al. ............. 514/368

FOREIGN PATENT DOCUMENTS

| WO | WO 00/63703 A1 | 10/2000 | |
|---|---|---|---|
| WO | 00/63703 | * 10/2000 | .......... G01N/33/92 |

OTHER PUBLICATIONS

Kramer, W. et al., "Intestinal Bile Acid Absorption—Na$_+$—Dependent Bile Acid Transport Activity in Rabbit Small Intestine Correlates with the Coexpression of an Integral 93–kDa and Pcripheral 14–kDa Bile Acid—Binding Membrane Protein along the Duodenum–Illeum Axis", The Journal of Biological Chemistry, 1993, pp. 18035–18046, vol. 268, No. 24, Issue of Aug. 25, The American Society for Biochemistry and Molecular Biology, Inc., USA.

Davis, H. R. et al., "Effect of the cholesterol absorption inhibitor SCH48461 in combination with the HMG–CoA reductase inhibitor lovastatin in rabbits, dogs and rhesus monkeys", Atherosclerosis X—Proceedings of the 10th International Symposium on Atherosclerosis, Oct. 1994, pp. 162–163, Montreal.

Mcateer, J. A. et al., "Basic cell culture technique and the maintenance of cell lines", Basic Cell Culture: A Practical Approach, 1994, pp. 93–122, IRL press.

Steinberg, D., "Oxidized LDL, Its Receptors, and Its Role in Atherosclerosis", XII International Symposium on Drugs Affecting Lipid Metabolism, 1995, pp. 1–15, Netherlands.

Patricia A. Detmers et al., "A target for cholesterol absorption in the enterocyte brush border membrane", Biochimica et Biophysica Acta, 2000, pp. 243–252, vol. 1486.

Helmut Hauser et al., "Identification of a Receptor Mediating Absorption of Dietary Cholesterol in the Intestine", Biochemistry, 1998, pp. 17843–17850, vol. 37.

Melba Hernandez et al., "Intestinal absorption of cholesterol is mediated by a saturable inhibitable transporter", Biochimica et Biophysica Acta, 2000, pp. 232–243, vol. 1486.

Susan L. Acton et al., "Expression Cloning of SR–BI, a CD36–related Class B Scavenger Receptor", The Journal of Biological Chemistry, 1994, pp. 21003–21009, vol. 269, No. 33.

* cited by examiner

*Primary Examiner*—Christopher R. Tate
*Assistant Examiner*—Maury Audet
(74) *Attorney, Agent, or Firm*—Heller Ehrman White and McAuliffe

(57) ABSTRACT

The invention relates to a vertebrate intestinal protein which absorbs cholesterol. It was possible to identify the protein by means of high-affinity crosslinking compounds. The invention further relates to this use of the protein for carrying out a method for identifying a compound which inhibits cholesterol absorption in the intestine.

21 Claims, 2 Drawing Sheets

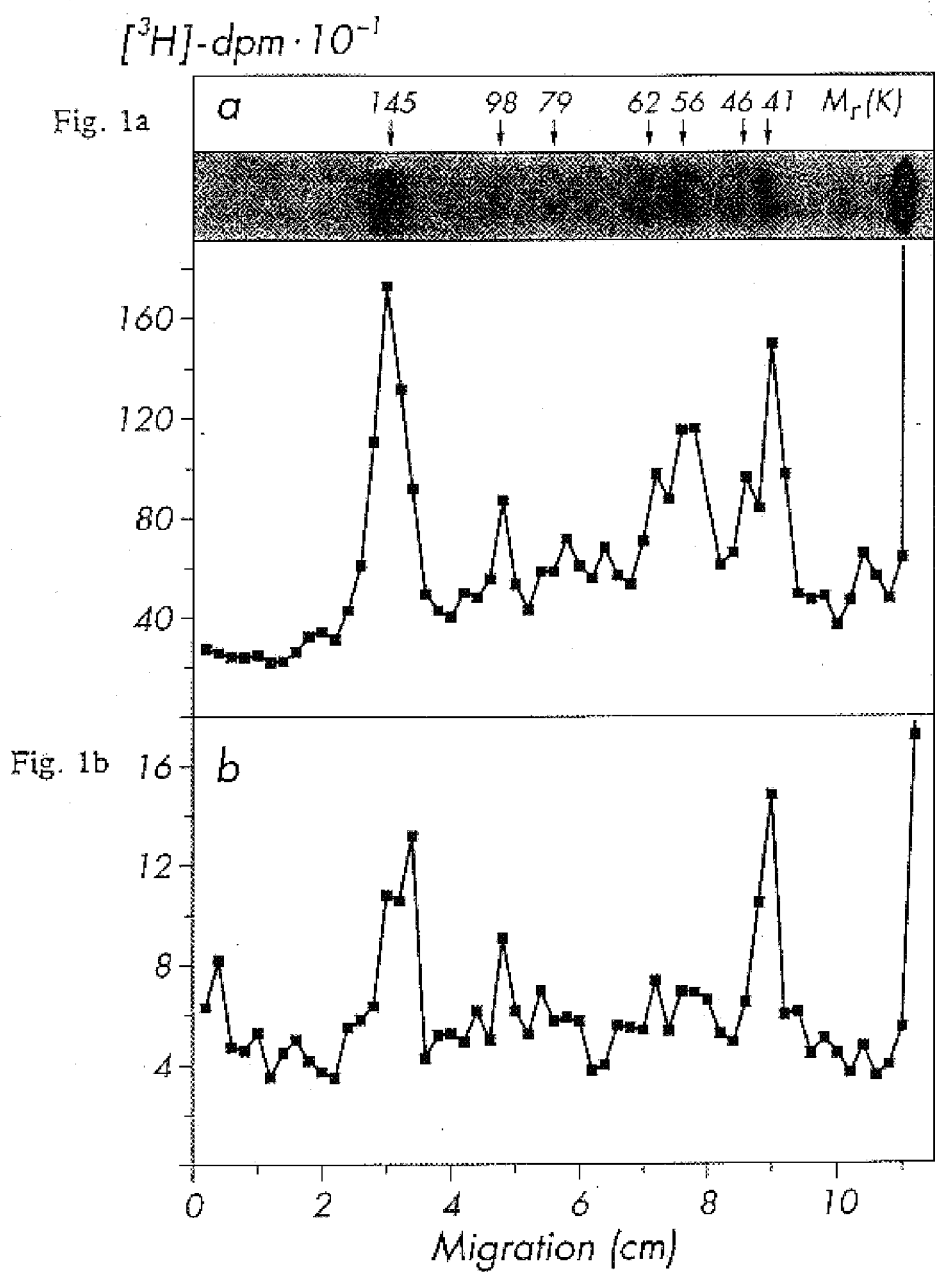

VERTEBRATE INTESTINAL PROTEIN WHICH ABSORBS CHOLESTEROL, ITS INHIBITORS AND MEHTOD OF IDENTIFYING THE SAME

CROSS REFERENCE TO RELATED APPLICATIONS

This application claims priority under 35 U.S.C. §119 to DE 100 42 447.3, filed Aug. 29, 2000, which is incorporated herein by reference in its entirety.

BACKGROUND OF THE INVENTION

The invention relates to a vertebrate intestinal protein which absorbs cholesterol. The protein is identified by means of high-affinity crosslinking compounds. The invention further relates to the use of the protein for carrying out a method for identifying a compound which inhibits cholesterol transport in the intestine.

In humans, on average about 50% of the cholesterol is present in the lumen of the intestine. The intraluminal cholesterol originates mainly from the diet and from the bile. About 2 g of cholesterol a day is discharged from the bile. The intestinal cholesterol absorption depends greatly on the presence of bile salts. Thus the effect of administration of inhibitors of the reuptake of bile salts or of bile salt sequestrants is to inhibit intestinal cholesterol absorption.

Inhibition of intestinal cholesterol absorption is an important aim of the treatment of lipid disorders, atherosclerosis and cardiovascular disorders. The prevailing opinion amongst experts is that intestinal cholesterol absorption takes place by physicochemical diffusion.

A number of observations in connection with cholesterol transport which indicate that a protein is involved are known. Intestinal cholesterol absorption is subject to great individual variability. Biochemical data from in vitro experiments indicate that proteins are involved in cholesterol exchange between small unilamellar vesicles and the brush border vesicles of the intestine. It was possible to observe large differences in the intestinal absorption of plant sterols such as β-sitosterol and campesterol, which differ only in a methyl group (β-sitosterol) and an ethyl group (campesterol). In humans, β-sitosterol showed inter alia an inhibition of cholesterol absorption. There are two highly active classes of compounds which inhibit intestinal cholesterol absorption on luminal administration. The compounds are, on the one hand, compounds derived from saponin, such as tiqueside and pamaqueside, and on the other hand certain derivatives of 2-azetidinones. Derivatives of 2-azetidinones as inhibitors of cholesterol absorption are described in Clader et al., J. Med. Chem. 39, 3684–3693, 1996. For the purposes of this invention, absorption is intended to mean attachment of a substance to a protein and transport of this substance with the aid of this protein.

Several proteins have to date been thought to be associated with cholesterol absorption. However, as yet no protein unambiguously involved in cholesterol absorption in the intestine has been described. This leads to a number of disadvantages in the search for a rational procedure for identifying specific inhibitors of intestinal cholesterol absorption. This is of particular importance also because inhibitors of intestinal cholesterol absorption are especially suitable for the treatment of all types of lipid disorders, atherosclerosis and cardiovascular disorders. Cholesterol is distributed uniformly in all cells both in the lipid bilayer of the membranes and in lipid vesicles. Transport measurements with vesicles or cells are therefore very complex and subject to interference.

It is therefore an object of the present invention to provide a protein which is involved in intestinal cholesterol absorption.

SUMMARY OF THE INVENTION

Accordingly, in one embodiment, the instant invention provides an isolated cholesterol-absorbing protein from intestinal tissue of a mammalian organism which has been obtained by a process comprising: a) detecting said protein by contacting intestinal cells or parts of intestinal cells of a mammalian organism with a radiolabeled compound which acts as an inhibitor of intestinal cholesterol absorption, wherein said compound comprises a photolabile group; and b) isolating said protein.

In another embodiment, the instant invention also provides a pharmaceutical composition comprising a cholesterol-absorbing protein and a pharmaceutically acceptable excipient.

In another embodiment, the instant invention also provides a method of inhibiting cholesterol uptake comprising administering to a patient in need thereof an effective amount of a cholesterol-absorbing protein.

In another embodiment, the instant invention also provides a method of treating a disorder of cholesterol uptake or cholesterol excretion, lipid disorders, atherosclerosis, or cardiovascular disorders comprising administering to a patient in need thereof an effective amount of a cholesterol-absorbing protein.

In another embodiment, the instant invention also provides a method for identifying a compound which inhibits intestinal cholesterol absorption, comprising: a) contacting a cholesterol-absorbing protein from an intestinal tissue of a mammalian organism with a test compound; and b) detecting binding of said compound to said protein, whereby compounds that bind to said protein are identified as inhibitors of intestinal cholesterol absorption. Preferably, the method comprises contacting intestinal cells or parts of intestinal cells comprising a cholesterol-absorbing protein with a test compound.

In another embodiment, the instant invention provides compounds that are inhibitors of cholesterol-absorbing proteins.

In another embodiment, the instant invention provides a pharmaceutical composition comprising an effective amount of one or more compounds of the instant invention and a pharmaceutically acceptable excipient.

In another embodiment, the instant invention provides a method of inhibiting cholesterol uptake comprising administering to a patient in need thereof an effective amount of one or more compounds of the instant invention.

In another embodiment, the instant invention provides a method of treating a disorder of cholesterol uptake or cholesterol excretion, lipid disorders, atherosclerosis, or cardiovascular disorders comprising administering to a patient in need thereof an effective amount of one or more compounds of the instant invention.

In another embodiment, the instant invention provides a method for detecting the presence of a cholesterol-absorbing protein, comprising: a) contacting a protein with a compound according to the invention that binds the protein; b) detecting binding of said compound to said protein, whereby a protein that binds to said compound is identified as a cholesterol-absorbing protein.

In another embodiment, the instant invention provides a diagnostic kit for an assay for detecting the presence of a cholesterol-absorbing protein comprising one or more compounds of the instant invention.

In another embodiment, the instant invention provides a chemical conjugate comprising a polymer covalently linked to an inhibitor of intestinal cholesterol-absorption. Preferably, the polymer is covalently linked to a compound of the instant invention, further comprising a cholesterol-absorbing protein connected thereto.

In another embodiment, the instant invention provides a method for obtaining a cholesterol-absorbing protein, comprising: a) contacting parts of a disrupted cell comprising a cholesterol-absorbing protein with a chemical conjugate according to the instant invention to form a conjugate comprising a polymer covalently linked to an inhibitor of intestinal cholesterol-absorption and a cholesterol-absorbing protein connected thereto; and b) separating said cholesterol-absorbing protein from said conjugate to obtain said cholesterol-absorbing protein.

In another embodiment, the instant invention provides precursors of inhibitors of cholesterol-absorbing protein.

Additional objects, features and advantages of the invention will be set forth in the description which follows, and in part, will be obvious from the description, or may be learned by practice of the invention. The objects, features and advantages of the invention may be realized and obtained by means of the instrumentalities and combination particularly pointed out in the appended claims.

BRIEF DESCRIPTION OF THE DRAWINGS

The accompanying drawings, which are incorporated in and constitute a part of the specification, illustrate a presently preferred embodiment of the invention, and, together with the general description given above and the detailed description of the preferred embodiment given below, serve to explain the principles of the invention.

FIG. 1a, FIG. 1b: Labeling of proteins of rabbit brush border membrane with radiolabeled compounds of the formula I or II. The proteins were precipitated and fractionated on an SDS polyacrylamide gel. The amount of radioactivity was determined by quantitative fluorography. The distance from the application point in cm is plotted on the horizontal axis of the diagram, and the result of counting in $^3$H dpm is plotted on the vertical axis. FIG. 1a shows in the upper part the distribution of the radioactivity after labeling with radiolabeled compound of the formula II and fluorographic detection. A compound of the formula I was used for labeling in FIG. 1a, and a compound of the formula II was used in FIG. 1b. Specifically labeled proteins are evident from the peaks.

DETAILED DESCRIPTION OF THE PREFERRED EMBODIMENTS

Figure 2A:
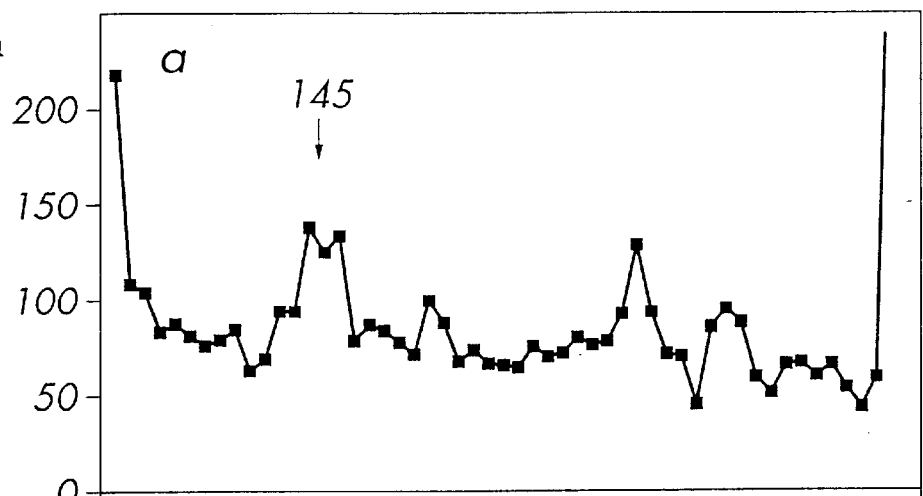
FIGS. 2a, 2b: Rabbits were fed for 10 days with a diet containing high concentrations of cholesterol. Then vesicles from the brush border membranes of these animals were prepared and subsequently labeled by a compound of the formula I or II as described, and then the proteins were precipitated and fractionated on an SDS polyacrylamide gel. The amount of radioactivity was determined by quantitative fluorography. The distance from the application point in cm is plotted on the horizontal axis of the diagram, and the result of counting in $^3$H dpm is plotted on the vertical axis. A compound of the formula I was used for labeling in FIG. 2a, and a compound of the formula II was used in FIG. 2b. A specific labeling of a protein with a molecular weight of 145 kDa was obtained.

In one embodiment, the invention therefore relates to a cholesterol-absorbing protein from the intestinal tissue of a mammalian organism. In one preferred embodiment, the cholesterol-absorbing protein may be obtained by the following process steps:

a) providing intestinal cells or parts of these intestinal cells of a mammalian organism, b) providing a radiolabeled compound which acts as inhibitor of intestinal cholesterol absorption and contains a photolabile group, c) contacting the intestinal cells or parts of these intestinal cells from a) with a compound from b)

d) irradiation of the mixture from c) with UV light, e) disruption of the cells after irradiation as in d), f) fractionation of the components of the disrupted cells after disruption as in e), g) detection, after fractionation as in f), of a protein which contains a bound compound from b).

The intestinal cells can be provided, for example, by dissection of the intestine from animals and subsequent purification, enzymatic disruption of the connective tissue and suspension of single cells in isotonic buffer solutions. Intestinal tissues suitable for the provision of intestinal cells are, inter alia, the corresponding parts of animals remaining after slaughtering. Intestinal cells can also be provided from human intestinal tissue after parts of the intestine have been obtained at operation. The intestinal cells can also consist of intestinal cell cultures provided for the purpose of the invention by application of cell culture techniques. Parts of intestinal cells may be organelles of the intestinal cells. Organelles are, preferably, membranes of the intestinal cells. Membranes of the intestinal cells can be obtained by differential centrifugation after disruption of these cells. Parts of intestinal cells are, preferably, also protein fractions. Provision of intestinal cells or parts of intestinal cells are familiar to the skilled worker, in this case a biochemist. Reference is made in particular to the following textbooks: "Basic Cell Culture, A practical approach, IRL press (1994), Editor: J. M. Davis" and "Current Protocols in Protein Science, John Wiley & Sons (2000), Editors: J. E. Coligan, B. M. Dunn, H. L. Ploegh, D. W. Speicher, P. T. Wingfield".

In a preferred embodiment of the invention, intestinal cells from humans, monkeys, cattle, pigs, rats, mice, rabbits or hamsters are used.

A preferable compound used as an inhibitor of intestinal cholesterol absorption and containing a photolabile group is the following compound of the formula 1, which may also be radiolabeled.

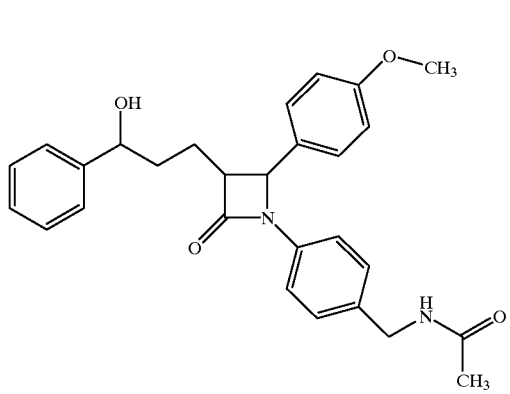

I

The name of the compound of the formula I is N-{4-[3-(3-hydroxy-3-phenylpropyl)-2-(4-methoxyphenyl)-4-oxoazetidin-1-yl]benzyl}acetamide.

Another preferred compound which is an inhibitor of intestinal cholesterol absorption and which contains a photolabile group is the following compound of the formula II, which may also be radiolabeled.

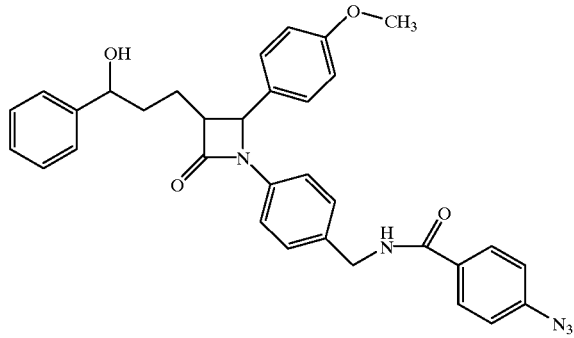

The name of the compound of the formula II is 4-azido-N-{4-[3-(3-hydroxy-3-phenyl-propyl)-2-(4-methoxyphenyl)-4-oxoazetidin-1-yl]benzyl}benzamide.

Another preferred compound which acts as an inhibitor of intestinal cholesterol absorption and which contains a photolabile group is the following compound of the formula III, which may also be radiolabeled.

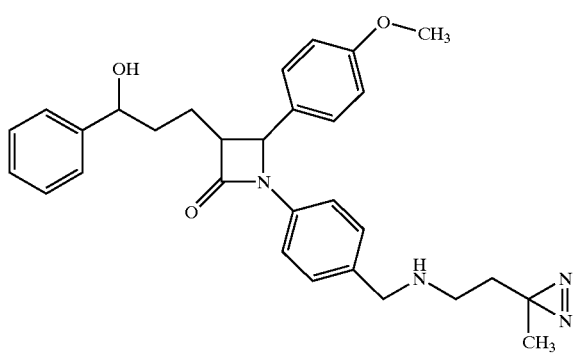

The name of the compound of the formula III is 3-(3-hydroxy-3-phenylpropyl)-4-(4-methoxyphenyl)-1-(4-{[2-(3-methyl-3H-diazirin-3-yl) ethylamino]methyl}phenyl)-azetidin-2-one.

The synthesis of a compound of the formula I, II and III is described in the examples hereinafter.

The protein of the invention is able to preferentially bind an inhibitor of intestinal cholesterol absorption. The protein preferably binds azetidinones or saponins. It is also preferred for the protein to be able to bind cholesterol. The inhibition of intestinal cholesterol absorption is determined, for example, using isolated human or animal intestinal cells, intestinal cell lines or parts of a human or animal intestine. This is done by determining the absorption onto said cells using labeled cholesterol. The label on the cholesterol may consist of a radiolabel or another label. It is possible to use as radiolabel $^3H$, $^{14}C$ or other isotopes which can be inserted into the molecular structure of cholesterol by synthetic methods known to the skilled worker. An inhibitor of intestinal cholesterol absorption reduces the amount of cholesterol absorbed by the intestinal cells.

In one embodiment of the invention, the protein or parts thereof have a size of from about 150 to about 25 kDa. In a particularly preferred embodiment, the protein or parts thereof have a size of from about 150 kDa to about 32 kDa. In another particularly preferred embodiment, the protein or parts thereof have a size of from about 150 kDa to about 42 kDa. In a very particularly preferred embodiment, the protein, in particular a part thereof, has a size of about 145 kDa, preferably 145 kDa.

In another embodiment of the invention, the protein or parts thereof have a size of from 150 to 25 kDa. In a particularly preferred embodiment, the protein or parts thereof have a size of from 150 kDa to 32 kDa. In another particularly preferred embodiment, the protein or parts thereof have a size of from 150 kDa to 42 kDa. In a very particularly preferred embodiment, the protein, in particular a part thereof, has a size of 145 kDa.

The described difference in the sizes of the protein of this invention may arise through initial formation of a precursor protein which is split up by a subsequent processing into parts differing in size. Parts of the protein may be produced by enzymatic or nonenzymatic cleavage, disintegration of the protein during the experimental workup or other processes.

Preferred proteins of this invention have a size of 140–150 or about 140–150 kDa, 145 kDa, 97 kDa, 90 kDa, 80 kDa, 72 kDa, 65 kDa, 63 kDa, 60 kDa, 58 kDa, 43 kDa, 41 kDa, 36 kDa, 33 kDa, 32 kDa or 25 kDa. In further preferred embodiments, the protein has a size of 140–150 or about 140–150 kDa, 145 kDa, 97 kDa, 90 kDa, 87 kDa, 80 kDa or 41 kDa. In other embodiments again the protein has a size of 140–150 or about 140–150 kDa, 145 kDa, 97 kDa, 58 kDa, 32 kDa. In the particularly preferred embodiment, the protein has a size of about 145 kDa, preferably 145 kDa.

The size of the protein can be determined using well-known techniques, for example, by using denaturing polyacrylamide gel electrophoresis comparing with size markers, by high pressure liquid chromatography comparing with size markers, gel chromatography comparing with size markers, mass spectrometry or other methods.

In a preferred embodiment, the protein is glycosylated. This glycosylated form of a protein is identified through the size of the protein decreasing when the protein is treated with a glycosidase. Details of suitable methods for checking glycosylation are to be found by the skilled worker in "Carbohydrate Biotechnology Protocols, Methods in Biotechnology, 10 (1999) Humana Press, ISBN 0-89603-563-8, Editor C. Bucke".

The contacting of the intestinal cells or of parts of these intestinal cells, preferably membranes, with the radiolabeled compound comprising an inhibitor of intestinal cholesterol absorption and a photolabile group can take place in conventional laboratory containers such as, for example Eppendorf vessels, centrifuged tubes or glass flasks. The underlying medium contains, for example, buffer substances, nutrient medium components, salts, trace elements and others in aqueous solution.

A photolabile group in a molecule can be used to produce covalent linkages to a molecule, preferably a protein, located in the direct vicinity. For this purpose, the compound with the photolabile group is initially brought into the direct vicinity of the molecule to which the covalent connection is to be produced. This can take place, for example, through another part of the compound which acts as a specific inhibitor of a protein, preferably an inhibitor of cholesterol absorption. Contacting the compound with the molecule is followed by irradiation with UV light. The irradiation with UV light activates the photolabile group and initiates the production of a covalent connection to the interacting molecule, in particular to a protein. Suitable as photolabile group are, for example, diazirine, azido or carbonyl functional groups.

Preferably, it is possible to employ for the irradiation a conventional UV lamp like that used, for example, for visualizing polynucleotides with intercalated ethidium bromide or for sterilizing laboratory surfaces, or a photochemical reactor (obtainable inter alia from "The Southern Ultraviolet Company, Hamden, Conn.") The disruption of the cells after irradiation with UV light is carried out using methods normally used for cell disruption. Examples thereof are repeated freezing and thawing, treatment of the cells with ultrasound, the use of a French press or the addition of a detergent and enzymes. The fractionation of the proteins of the cell lysate can be carried out, for example, by precipitation with ammonium sulfate, by differential centrifugation or application of chromatographic techniques. Chromatographic techniques suitable for this purpose are, for example, denaturing or nondenaturing polyacrylamide gel electrophoresis in one or two dimensions, high pressure liquid chromatography, ion exchange chromatography or affinity chromatography. These techniques are familiar to the skilled worker and are dealt with in detail for example in the previously mentioned "Current Protocols in Protein Science".

Preferably, the detection of a protein after a fractionation takes place by means of the radiolabeling of the compound containing an inhibitor of intestinal cholesterol absorption and a photolabile group. A radioactive isotope which can be used for this purpose is, for example, $^3$H or $^{14}$C. A suitable detection method is, for example, detection of the protein which contains a covalently bonded compound by means of a film material used for X-ray photography after the protein has been introduced onto a polyacrylamide gel with the aid of polyacrylamide gel electrophoresis. Other suitable detection methods are liquid scintillation counting or flat bed scanning.

In another embodiment, the invention further relates to a pharmaceutical composition comprising a protein of the invention. This pharmaceutical can be used, for example, for the treatment of a disorder of cholesterol uptake or cholesterol excretion, of lipid disorders, atherosclerosis or cardiovascular disorders or to enhance cholesterol absorption. The pharmaceutical may contain other substances or excipients which may be beneficial, for example, to stabilize or formulate the pharmaceutical. Such substances and excipients are commonly known and described, for example, in *Remingtons* Pharmaceutical Sciences, fifth edition, by Mack Publishing Company, which is incorporated herein by reference in its entirety. The protein in the pharmaceutical composition can bind cholesterol in the intestine.

In another embodiment, the invention also relates to the use of a protein as described above for the production of a pharmaceutical composition for the treatment of a disorder of cholesterol uptake or cholesterol excretion, of lipid disorders, atherosclerosis or cardiovascular disorders.

In another embodiment, the invention further relates to a method for identifying a compound which inhibits intestinal cholesterol absorption, wherein the method may comprise the following process steps:
a) provision of a protein of this invention,
b) provision of a compound,
c) contacting a protein from a) with a compound from b),
d) determination of the binding of the compound from b) to the protein from a).

A protein of the invention for carrying out a method as described above may be provided from all cells which produce such a protein and, preferably cells from the brush border of the intestinal tissue of mammalian organisms. Mammalian organisms from which these intestinal cells are obtained preferably include, but are not limited to humans, monkeys, cattle, pigs, rats, mice, rabbits, hamsters or another vertebrate species. These cells may be provided by preparing cell suspensions from the brush border tissue of the intestine of such organisms. Suitable intestinal material is obtained, for example, by surgical procedures. Other sources may derive from the parts of animals remaining after slaughtering. Cells of an intestinal cell line are equally suitable. To prepare suitable cell preparations, the intestinal tissue may be subjected to an enzyme treatment to release single cells and then undergo differential centrifugation. The resulting cells or organelles are subsequently taken up in suitable aqueous media. These aqueous media may contain buffer substances, salts, proteins and, in addition, excipients.

Proteins for carrying out the method may also be provided from an in vitro system. For this purpose, a protein of this invention may be obtained from cells, for example of the brush border of the intestine of mammalian organisms, with the aid of chromatographic techniques. The provision of a compound for the aforementioned method takes place, for example, by chemical synthesis. The compound may be part of a collection of chemical compounds like those resulting from storage and cataloging of the chemical compounds from completed synthesis programs (called "compound libraries"). The compound may in other cases have been produced by a microorganism, in particular a bacterium, a fungus or an animal or plant species (natural substances). In the case of a natural substance, the provision can also take place by isolation from the appropriate organisms. The contacting of a protein with a compound to carry out the method frequently takes place in aqueous solutions to which a certain proportion of a solvent such as, for example, dimethyl sulfoxide or ethanol can be admixed. The aqueous solutions usually also contain buffer substances, ions or stabilizing additions such as proteins, glycerol or others. Particular constant conditions, for example for the temperature, the pH, the ionic conditions, the concentration of the protein or of the compound, or the volume, may be advantageous for the contacting. Thus, for example, it may be preferable to keep the temperature constant at 37° C. or at room temperature during the contacting. The determination of the binding of the compound to the protein after carrying out the contacting takes place, for example, by interaction with cholesterol which is radiolabeled or labeled in another way, using the displacement of the cholesterol as a measure of the affinity of the compound for the protein.

In another preferred embodiment, the invention relates to a method for removing cholesterol from food being digested by administering a cholesterol-absorbing protein of the invention to a subject.

In another preferred embodiment, the invention relates to a method for removing cholesterol from body fluids of a subject by contacting the body fluids with a protein of the instant invention.

In another embodiment, the invention relates to a pharmaceutical composition which comprises a compound or more than one compound identified as an intestinal cholesterol inhibitor using a method for identifying a compound which inhibits intestinal cholesterol absorption as provided herein. The invention further relates to the use of a compound which has been identified by the method of the instant invention for producing a pharmaceutical composition for the treatment of a disorder of cholesterol uptake or cholesterol excretion, of lipid disorders, atherosclerosis or cardiovascular disorders.

In another embodiment, the invention also relates to a method for obtaining a protein of the invention, where the method may comprise the following process steps:
a) providing a cell comprising a protein of the invention,
b) providing a chemical conjugate comprising a polymer, where the polymer is possibly covalently linked via a spacer to an inhibitor of intestinal cholesterol absorption,
c) disruption of the cell from a)
d) contacting the disrupted cell from c) with a chemical conjugate from b),
e) separation of the unbound proteins and other molecules of the disrupted material from c) from the chemical conjugate,
f) elution of the proteins which have entered into a stable connection with chemical conjugate after contacting as in d) and, where appropriate, further purification.

Preferably, a vertebrate intestinal cell may be used as a cell comprising a protein of the instant invention. Preferable mammalian organisms, from which such intestinal cells are obtained, include for example humans, monkeys, cattle, pigs, rats, mice, rabbits or hamsters. The cells may be obtained by preparing cell suspensions from the brush border tissue of the intestine. Suitable intestinal material is obtained, for example, by surgical procedures. Other sources may be parts of animals remaining behind after slaughtering. Cells of an intestinal cell line are also suitable. To release single cells, the intestinal tissues, for example, are subjected to an enzyme treatment or a differential centrifugation. The resulting preparations of the cells or organelles are then taken up in suitable aqueous media. These aqueous media may contain buffer substances, salts, proteins and, in addition, excipients. The cell preparation is subjected to a disruption in order to obtain a protein of this invention. The disruption of the cells is carried out using the methods normally used for cell disruption. Examples thereof are repeated freezing and thawing, treatment of the cells with ultrasound, the use of a French press or the addition of a detergent and enzymes.

A chemical conjugate consisting of a polymer, wherein the polymer may be covalently linked via a spacer to an inhibitor of intestinal cholesterol absorption, may be provided by chemical synthesis. After the synthesis, the conjugate is taken up in an aqueous or organic solvent. Stable connection of a protein to this chemical conjugate can take place by affinity binding, via a hydrophilic or hydrophobic interaction or in another way. This connection of the protein to the chemical conjugate can be dissolved again by introducing suitable eluents. Such suitable eluents contain, for example, high concentrations of a substance which behaves as competitor with an affinity or other interaction.

The disrupted cells, which may be produced as just described, are contacted with the chemical conjugate. For this purpose, the chemical conjugate can be introduced as a suspension into a chromatography column beforehand. After packing the column, the disrupted material may then be loaded onto an affinity chromatography material and eluted with an aqueous solvent which may contain buffer substances, salts, proteins and excipients, in particular stabilizers, solubilizers or preservatives. The elution separates the unbound proteins and other molecules, which do not correspond to a protein of the instant invention from the chemical conjugate. The proteins which have entered into a stable connection with the chemical conjugate after contacting with the disrupted material are then eluted. This can take place, for example, by using increasing concentrations of the inhibitor which is present in the chemical conjugate. An alternative possibility is to use another inhibitor of intestinal cholesterol absorption. The eluted proteins can be subjected to another purification, for example by other chromatographic techniques such as ion exchange chromatography, polyacrylamide gel electrophoresis, gel chromatography, high pressure liquid chromatography.

In a preferred method for obtaining a protein of the invention as described above, the chemical conjugate comprises a polymer, where appropriate a linker, and an inhibitor of cholesterol absorption from the saponin or 2-azetidinone series, and preferably, a compound of the formula I, II or III of this invention or a combination thereof.

The invention further relates to a chemical conjugate comprising a polymer, wherein the polymer is preferably covalently linked via a spacer to an inhibitor of intestinal cholesterol absorption. Such an inhibitor is, in a preferred embodiment, a saponin or a compound of the formula I, II or III.

The invention further relates to a chemical conjugate of this invention, this conjugate comprising a bound protein of this invention.

The preparation of a chemical conjugate by chemical synthesis is described in the examples.

The invention relates to a compound of the formula I.

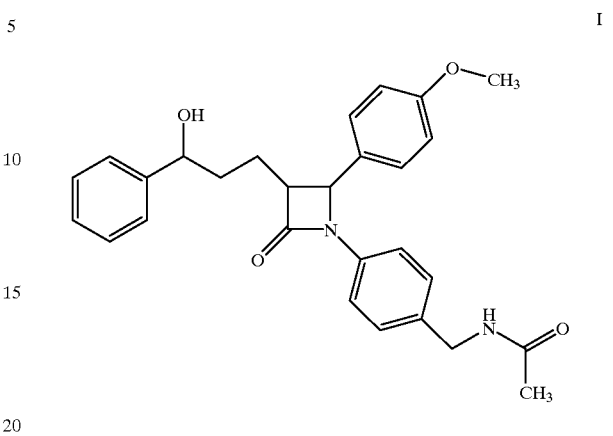

I

The invention further relates to a compound of the formula II.

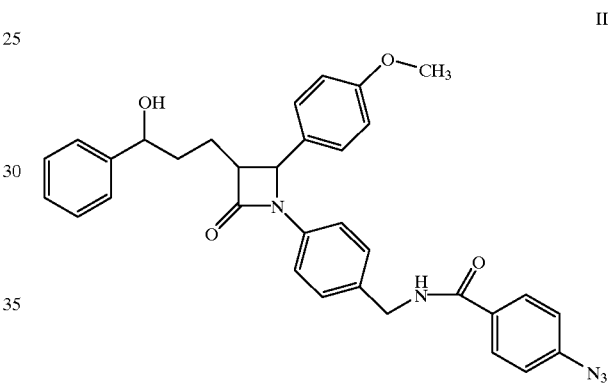

II

The invention also relates to a compound of the formula III.

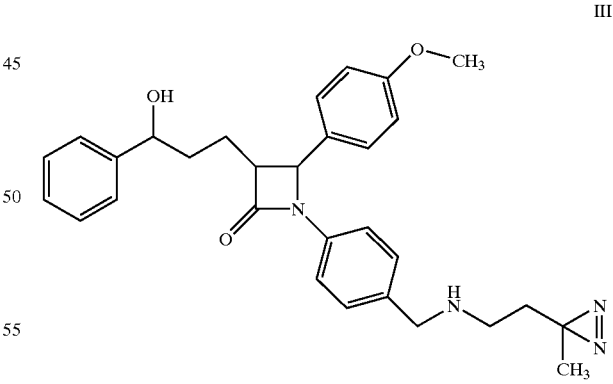

III

A compound of the formula I, II or III can be used to detect a protein of this invention (photolabel). A compound of the formula I, II or III is also suitable as inhibitor of a cholesterol-absorbing protein. The present invention therefore also relates to a diagnostic kit which comprises at least one compound of the formula I, II or III, and reagents for carrying out an assay for detecting a protein of this invention.

The invention also relates to the compounds 4-[3-(3-bromo-3-phenylpropyl)-2-(4-methoxyphenyl)-4-oxoazetidin-1-yl]benzonitrile, 4-[3-(3-hydroxy-3-phenylpropyl)-2-(4-methoxyphenyl)-4-oxoazetidin-1-yl] benzonitrile or 1-(4-aminomethylphenyl)-3-(3-hydroxy-3-phenylpropyl)-4-(4-methoxyphenyl)azetidin-2-one. These compounds which have just been mentioned can be used to prepare a compound of the formula I, II or III. The invention further relates to a pharmaceutical composition comprising an effective amount of one or more of the above compounds and a pharmaceutically effective excipient. Such excipients are well known to the skilled artisan, as described above. The amount which is effective also can be adjusted depending upon the age, weight and condition of the subject, according to methods well known to the skilled artisan.

The present invention, thus generally described, will be understood more readily by reference to the following examples, which are provided by way of illustration and are not intended to be limiting of the present invention.

EXAMPLES

Inhibitors of intestinal cholesterol absorption were synthesized (compounds of the formula I, II or III). These compounds contain photolabile groups which can be crosslinked with other molecules, in particular proteins, by means of UV light, and are radiolabeled with a specific activity greater than 1 Ci/mmol. These compounds are used to identify a protein of intestinal cholesterol absorption.

Example 1
Photoaffinity and Binding Studies:

Vesicles from the brush border tissue of the small intestine of rabbits were isolated by methods known to the skilled worker (Kramer et al. J. Biol. Chem. 268, 18035-18046 (1993). The photoaffinity labeling using a radiolabeled compound of the formula I, II or III of this invention was carried out in a photochemical reactor of the Rayonet RPR-100 type (obtainable from "The Southern Ultraviolet Company, Hamden, Conn."). The brush border vesicles thereof (100 to 200 µg of protein) were incubated with one of the compounds in a volume of 200 µl in 10 mM Tris/Hepes buffer (pH 7.4), 100 mM NaCl, 100 mM mannitol at 20° C. in the dark for 5 min. In place of the brush border vesicles it is also possible to use organelles, in particular membranes thereof. The statements hereinafter apply correspondingly to these. The incubation in the dark was followed by irradiation with UV light of 254 nm for 20 seconds or 60 seconds. The brush border vesicles were then washed twice with the buffer mentioned. The proteins were precipitated by conventional techniques such as, for example, addition of ethanol, addition of a salt or detergent, heating, repeated freezing and thawing, or another suitable method known to the skilled worker, and fractionated by SDS polyacrylamide gel electrophoresis. The radiolabeled proteins were detectable by LSC or fluorography. The affinity of the labeled proteins from the brush border tissue for the compounds was in the range from 1 to 10 nM.

Identification of an intestinal protein which absorbs cholesterol.

Vesicles were prepared from brush border membranes of the rabbit intestine. They were labeled by means of a radiolabeled compound of the formula I, II or III. The proteins were precipitated and fractionated on an SDS polyacrylamide gel.

On use of the compound of the formula I it was possible to label proteins with a molecular weight of 145 kDa, 97 kDa, 72 kDa, 63 kDa, 58 kDa, 41 kDa 32 kDa and 25 kDa (FIG. 1a). With the compound of the formula II it was possible to label compounds with a molecular weight of 145 kDa, 97 kDa, 87 kDa and 41 kDa. The greatest incorporation was shown by the protein with the molecular weight of 145 kDa. It was possible to show by solubilization experiments with nonionic or zwitterionic detergents and sodium carbonate that the proteins with the molecular weight of 145 kDa, 97 kDa, 58 kDa and 32 kDa are integral membrane proteins. The molecular weights of the proteins are stated subject to a certain range of uncertainty which is caused by the SDS polyacrylamide gel electrophoresis method used, but is also known for other corresponding methods. The variations in the molecular weights are in the region of up to +/−10%. The stated values represent the means of a plurality of experiments. In the case of the protein with the stated molecular weight of 145 kDa, the determinations of the molecular weight in 10 experiments carried out independently of one another by SDS polyacrylamide gel electrophoresis resulted in a mean of 145.3 kDa with a standard deviation of +/−7.55 kDa.

Further photolabeling studies were carried out with known inhibitors of intestinal cholesterol absorption. Derivatives of S3302 were prepared for this purpose. The compound S3302 is a racemate of the cholesterol inhibitor SCH 48461. This compound very efficiently inhibits intestinal cholesterol absorption in rabbits, hamsters, dogs, rhesus monkeys and humans (Davis et al., Atherosclerosis 109, 162–163 (1994); Bergman et al.; XII International Symposium on Drugs affecting Lipid Metabolism; conference reports (1995)). The compound SCH 58235 (references just mentioned) shows in hamsters an effect which is increased 50-fold on direct comparison. This effect is explained by the introduction of an additional (3S)-hydroxyl group in position R2. It was possible to prepare an analogous hydrogen derivative of SCH 48461 (=S6503) which showed similar activity to SCH 58235 in an in vivo experiment. S6503 brings about, in analogy to its strong in vivo effect on cholesterol absorption, a greater inhibition, compared with S3302, of the labeling of the protein with the molecular weight of 145 kDa. None of the inhibitors of cholesterol absorption used showed a noteworthy effect on bile salts, glucose, oligopeptides, alanine, fatty acids or the $Na^+$/bile salt transport route in the in vivo experiments.

Figure 2B:
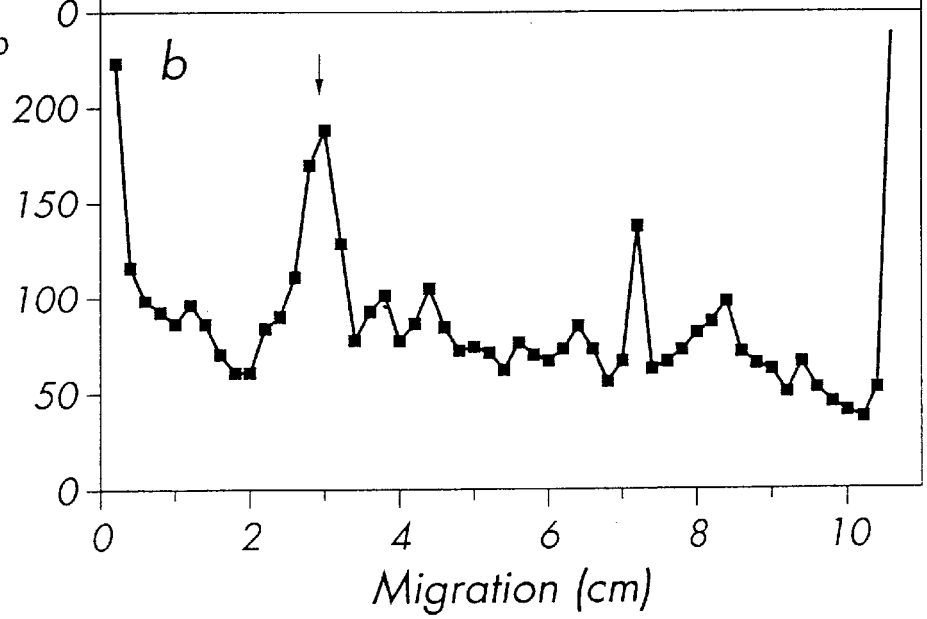

Photoaffinity studies with brush border membranes isolated from rabbits given a diet with large amounts of cholesterol for 10 days showed distinctly greater labeling of the protein with the molecular weight of 145 kDa (FIG. 2).

It is evident from the above statements that it was possible to prepare a protein which brings about intestinal cholesterol absorption. It was thus possible to achieve the object of this invention.

Example 2
Provision of a chemical conjugate of a polymer and a compound which acts as inhibitor of intestinal cholesterol absorption.

An aminoalkyl derivative of a compound which acts as inhibitor of intestinal cholesterol absorption (5–100 µmol), in particular a compound of the formula I, II or III of this invention, is dissolved in 1–5 ml buffer/0.1 M $NaHCO_3$/0.5 M NaCl (pH 8.3). Polymeric support materials containing activated carboxyl groups with or without spacer, such as, for example, a Hi-Trap column with an N-hydroxysuccinimidyl-activated hexylcarboxylic acid as spacer (Pharmacia Biotechnology) are prepared for conjugation in accordance with the manufacturer's instructions. The activated matrix is incubated with the above solution of an aminoalkyl derivative of a cholesterol absorption inhibitor for 0.5–5 h. Unreacted activated carboxyl groups are then neutralized by sequential washing several times with in each case 5–15 ml of the following buffers:

0.5 M ethanolamine/0.5 M NaCl (pH 8.3)

0.1 M sodium acetate/0.5 M NaCl (pH 4.0)

The conjugate column is then prepared for the affinity chromatography by washing with 10 mM sodium phosphate buffer (pH 7.4)/1% n-octyl glucoside.

Concentration of binding proteins for cholesterol absorption inhibitors by affinity chromatography.

Biological membranes from cells which contain cholesterol transport proteins (2–20 mg of protein), such as, for example, brush border membranes from intestinal cells, are solubilized at a protein concentration of 0.5–2.5 mg/ml in 10 mM sodium phosphate buffer (pH 7.4)/1% n-octyl glucoside at 4° C. for 1 h. After removal of remaining particulate material by centrifugation, the clear supernatant solution, which contains the solubilized membrane proteins, is loaded onto the conjugate column described above, and the elution of protein is followed by the UV absorption. After unretarded proteins have been washed out, the specific binding proteins for cholesterol absorption inhibitors which are adhering to the column are eluted by applying solutions which contain cholesterol absorption inhibitors in concentrations of 1–10 mM or which contain 1–5% of nonionic detergents such as Triton X-100. The binding proteins for cholesterol absorption inhibitors in these eluates are then separated by electrophoretic fractionation and their molecular size is determined. Their amino acid sequence can be determined by sequencing by methods familiar to the skilled worker by cutting out the appropriate protein bands, or antibodies against the individual proteins can be raised by subcutaneous deposition of the pieces of gel which contain the fractionated proteins in various animal species.

Example 3

The preparation of a compound of the formula I, II or III and of a radiolabeled derivative of a compound of the formula I, II or III is described below:

4-[3-(3-Bromo-3-phenyl propyl)-2-(4-methoxyphenyl)-4-oxoazetidin-1-yl]benzonitrile 16.0 g of 4-[2-(4-methoxyphenyl)-4-oxo-3-(3-phenylpropyl)azetidin-1-yl]benzonitrile are dissolved in 180 ml of tetrachloromethane, and 9.4 g of N-bromosuccinimide and 940 mg of benzoyl peroxide are added. The mixture is heated to reflux with stirring and monitored by thin-layer chromatography. The reaction is complete after about 30–50 min. The solution is mixed at room temperature with ethyl acetate and then washed with saturated sodium bisulfite solution and water, dried over sodium sulfate and concentrated in vacuo. The residue is purified on silica gel with ethyl acetate/heptane =1:2 as mobile phase. The bromide is obtained as a viscous oil. MS(FAB): 477 (M1+H$^+$), 475 (M2+H$^+$) [$C_{26}H_{23}BrN_2O_2$ M=475].

4-[3-(3-Hydroxy-3-phenylpropyl)-2-(4-methoxyphenyl)-4-oxoazetidin-1-yl]benzonitrile 17 g of 4-[3-(3-bromo-3-phenylpropyl)-2-(4-methoxyphenyl)-4-oxoazetidin-1-yl]-benzonitrile are dissolved in 500 ml of dioxane and, after addition of 34 ml of ~40 percent tetrabutylammonium trifluoroacetate solution, heated to reflux for 24 h. The mixture was concentrated to about half the volume, mixed with water and methyl tert-butyl ether and separated into the phases. The organic phase is concentrated, and the residue is stirred with 500 ml of ethanol and 200 ml of concentrated ammonia at room temp. for 1 h. It is then again concentrated in vacuo, and the crude product is purified on silica gel with dichloromethane/methanol =30:1 as mobile phase. The alcohol is obtained as an oil. MS (ESI): 413 (M+H$^+$), 395 (M+H$^+$-H$_2$O) [$C_{26}H_{24}N_2O_3$ M=412].

1-(4-Aminomethylphenyl)-3-(3-hydroxy-3-phenylpropyl)-4-(4-methoxyphenyl)-azetidin-2-one 7 g of 4-[3-(3-hydroxy-3-phenylpropyl)-2-(4-methoxyphenyl)-4-oxoazetidin-1-yl]-benzonitrile are dissolved in 200 ml of ethanol and, after addition of 15 ml of concentrated ammonia, hydrogenated with 7 g of 50% aqueous Raney nickel under 50 bar of hydrogen. The crude product obtained after removal of the catalyst by filtration with suction and removal of the solvent in vacuo is purified on silica gel with dichloromethane/methanol/ammonia =200:10:1. The amine is obtained. MS (FAB, +LiCl): 423 (M+Li$^+$) [$C_{26}H_{28}N_2O_3$ M=416].

4-Azido-N-{4-[3-(3-hydroxy-3-phenylpropyl)-2-(4-methoxyphenyl)-4-oxo-azetidin-1-yl]benzyl}benzamide 140 mg of 1-(4-aminomethylphenyl)-3-(3-hydroxy-3-phenylpropyl)-4-(4-methoxy-phenyl)azetidin-2-one are dissolved in 5 ml of dioxane, and 0.1 ml of tributylamine is added. To this mixture are added, under subdued light, 88 mg of 4-azidobenzoic acid succinimide ester, followed by stirring at room temperature for about 1 h. The crude product remaining after concentration is purified on silica gel with ethyl acetate/heptane =1:1 as mobile phase. MS (FAB): 562 (M+H$^+$), 544 (M+H$^+$-H$_2$O) [$C_{33}H_{31}N_5O_4$ M=561].

The radiolabeled benzamide is obtained analogously on a small scale in high dilution using tritium- or $^{14}$C-labeled azidobenzoic acid activated ester (from Amersham) and coelutes in a thin-layer chromatogram with unlabeled 4-azido-N-{4-[3-(3-hydroxy-3-phenylpropyl)-2-(4-methoxyphenyl)-4-oxoazetidin-1-yl]benzyl}benzamide.

N-{4-[3-(3-Hydroxy-3-phenylpropyl)-2-(4-methoxyphenyl)-4-oxoazetidin-1-yl]-benzyl}-acetamide 100 mg of 1-(4-aminomethylphenyl)-3-(3-hydroxy-3-phenylpropyl)-4-(4-methoxy-phenyl)azetidin-2-one are dissolved in 20 ml of methanol and, 0.3 ml of pyridine followed by 0.3 ml of acetic anhydride are added. The reaction is complete after 30 min at room temperature and, after concentration in vacuo, purification is carried out on silica gel with ethyl acetate as mobile phase. MS (ESI): 459(M+H$^+$), 441 (M+H$^+$-H$_2$O) [$C_{28}H_{30}N_2O_4$ M=458].

The radiolabeled acetamide is obtained analogously on a small scale in high dilution using tritium- or $^{14}$C-labeled acetic anhydride and coelutes with unlabeled N-{4-[3-(3-hydroxy-3-phenylpropyl)-2-(4-methoxyphenyl)-4-oxoazetidin-1-yl]benzyl}acetamide in a thin-layer chromatogram.

3-(3-Hydroxy-3-phenylpropyl)-4-(4-methoxyphenyl)-1-(4-{[2-(3-methyl-3H-diazirin-3-yl)ethylamino]methyl}phenyl)azetidin-2-one 100 mg of 1-(4-aminomethylphenyl)-3-(3-hydroxy-3-phenylpropyl)-4-(4-methoxy-phenyl)azetidin-2-one are dissolved in 5 ml of dimethylformamide and stirred with 2-(3-methyl-3H-diazirin-3-yl)ethyl toluene-4-sulfonate under subdued light at 60–70° C. for 6 h. Water is added and, after extraction with ethyl acetate, the solvent is removed in vacuo. Then dry toluene is added and the mixture is concentrated in vacuo twice. The crude product is purified on silica gel using dichloromethane/methanol =20:1 as mobile phase.

MS (ESI): 499 (M+H$^+$) [$C_{30}H_{34}N_4O_3$ M=498].

The radiolabeled azetidinone is obtained in the same way using tritium- or $^{14}$C-labeled diazirine and coelutes in a thin-layer chromatogram with unlabeled 3-(3-hydroxy-3-phenylpropyl)-4-(4-methoxyphenyl)-1-(4-{[2-(3-methyl-3H-diazirin-3-yl)ethylamino]methyl}phenyl)azetidin-2-one.

| Abbreviations: | |
| --- | --- |
| h | hour(s) |
| LSC | liquid scintillation counting |
| MS (FAB) | mass spectrum (fast atom bombardment) |

-continued

| Abbreviations: | |
|---|---|
| MS (ESI) | mass spectrum (electrospray ionization) |
| M | mass |

Additional advantages, features and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined bye the appended claims and their equivalents.

As used herein and in the following claims, articles such as "the", "a" and "an" can connote the singular or plural.

All documents referred to herein are specifically incorporated herein by reference in their entireties.

Priority application DE 10042447.3-44 filed Aug. 29, 2000, including its specification, drawings, claims, and abstract, is incorporated herein by reference in its entirety.

We claim:

1. A process of isolating a cholesterol-absorbing protein from a mammalian organism comprising:

a) contacting intestinal cells or parts of intestinal cells of the mammalian organism with a compound selected from the group consisting of:

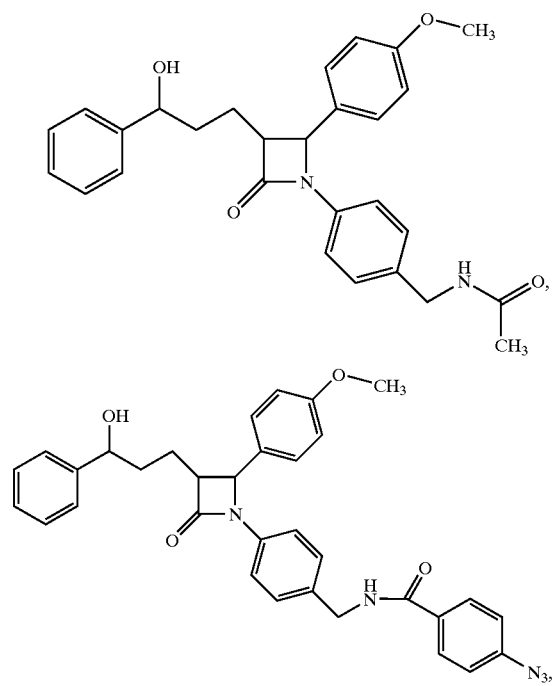

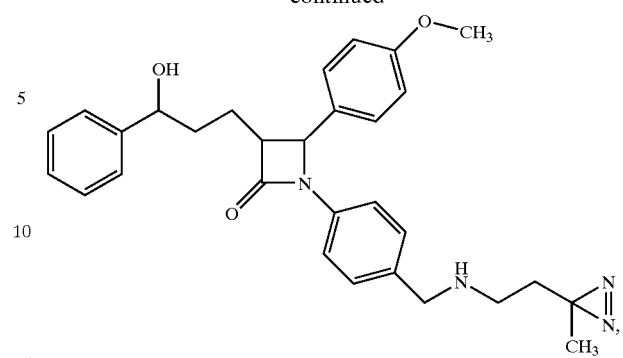

wherein said compound comprises a detectable label;

b) allowing said compound to bind a protein in said cells or parts of cells and detecting said binding c) isolating said protein bound to said compound, wherein said isolated protein is a cholesterol-absorbing protein.

2. The process of claim 1, wherein the intestinal cells originate from humans, monkeys, rats, cattle, pigs, mice, rabbits or hamsters.

3. The process of claim 1, wherein the compound is radiolabeled.

4. The process of claim 1, wherein the isolated protein is able to bind an inhibitor of intestinal cholesterol absorption.

5. The process of claim 1, wherein the isolated protein is able to bind azetidinones or saponins.

6. The process of claim 1, wherein the isolated protein is able to bind cholesterol.

7. The process of claim 1, wherein the isolated protein is from about 150 to about 25 kDa.

8. The process of claim 1, wherein the protein or is about 150 kDa to about 32 kDa.

9. The process of claim 1, wherein the isolated protein or is about 150 kDa to about 42 kDa.

10. The process of claim 1, wherein the isolated protein is about 145 kDa.

11. The process of claim 1, wherein the isolated protein is glycosylated.

12. A compound with a formula selected from the group consisting of:

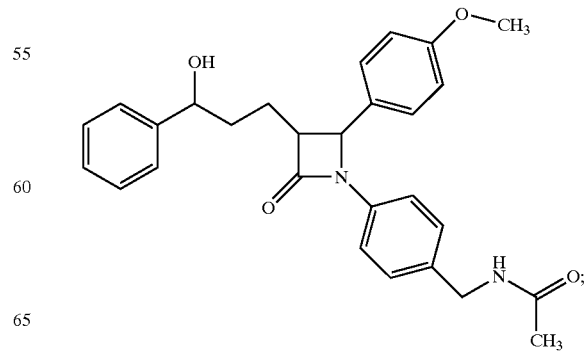

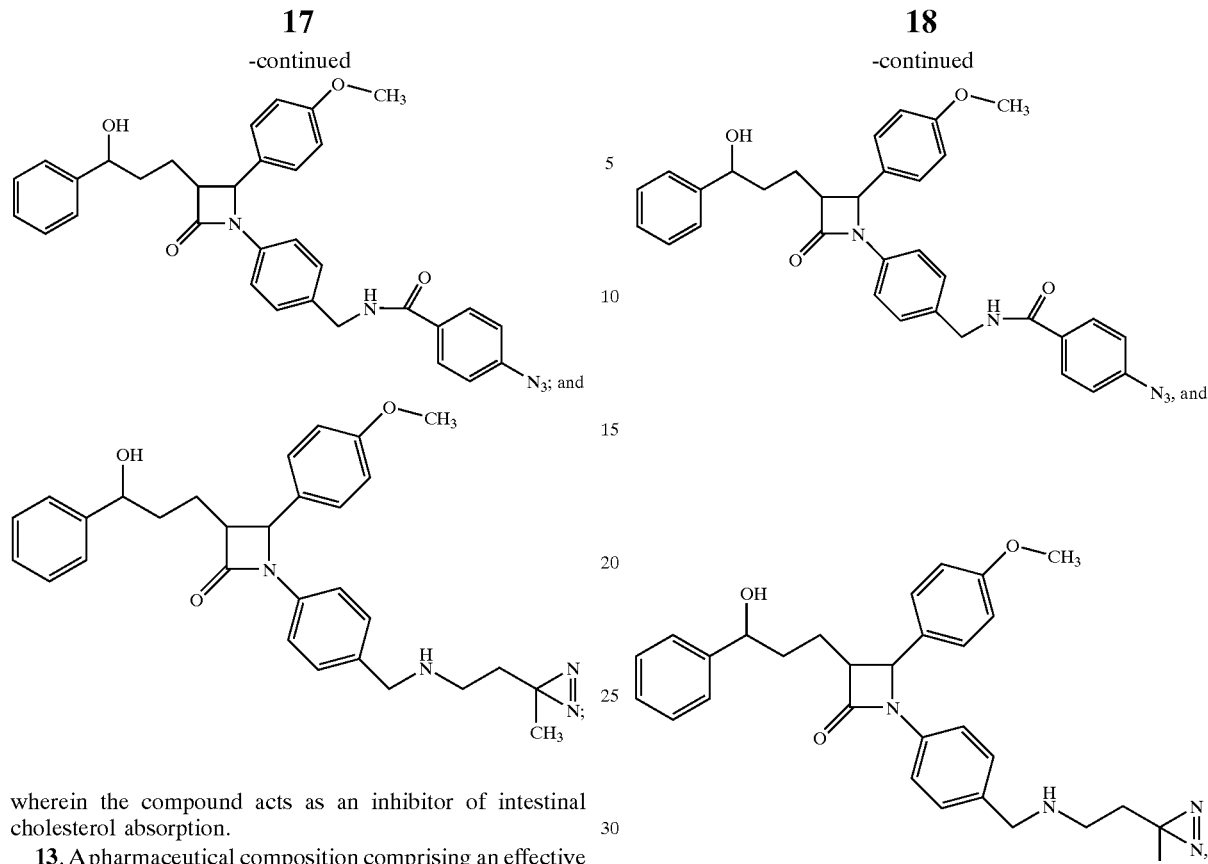

wherein the compound acts as an inhibitor of intestinal cholesterol absorption.

13. A pharmaceutical composition comprising an effective amount of one or more compounds according to claim 12 and a pharmaceutically acceptable excipient.

14. A method of inhibiting cholesterol uptake comprising administering to a patient in need thereof an effective amount of one or more compounds according to claim 12.

15. A method of treating a disorder of cholesterol uptake or cholesterol excretion, lipid disorders, atherosclerosis, or cardiovascular disorders comprising administering to a patient in need thereof an effective amount of one or more compounds according to claim 12.

16. A method for detecting the presence of a cholesterol-absorbing protein, comprising:

a) contacting a protein with a compound selected from the group consisting of:

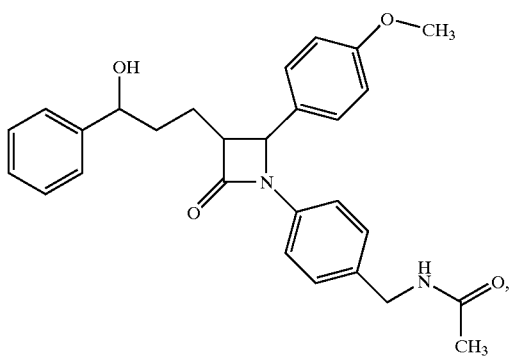

wherein said compound is detectably labeled;

b) allowing said compound to bind to the protein; and c) detecting binding of said compound to said protein, whereby a proteins that binds to said compound is identified as a cholesterol-absorbing protein.

17. The method of claim 16, wherein said protein is from an intestinal tissue of a mammalian organism.

18. The method of claim 16, wherein the protein is from about 150 to about 25 kDa.

19. The method of claim 16, wherein the protein is from about 150 kDa to about 32 kDa.

20. The method of claim 16, wherein the protein is from about 150 kDa to about 42 kDa.

21. The method of claim 16, wherein the protein is about 145 kDa.

* * * * *